(12) United States Patent
Davidson et al.

(10) Patent No.: US 11,497,816 B2
(45) Date of Patent: Nov. 15, 2022

(54) COMPOSITIONS AND METHODS FOR TREATING FRAGILE X SYNDROME AND RELATED SYNDROMES

(71) Applicant: The Children's Hospital of Philadelphia, Philadelphia, PA (US)

(72) Inventors: Beverly L. Davidson, Philadelphia, PA (US); Carolyn M. Yrigollen, Philadelphia, PA (US); Alejandro Monteys, Philadelphia, PA (US); Bryan Simpson, Philadelphia, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 352 days.

(21) Appl. No.: 15/766,423

(22) PCT Filed: Oct. 6, 2016

(86) PCT No.: PCT/US2016/055723
§ 371 (c)(1),
(2) Date: Apr. 6, 2018

(87) PCT Pub. No.: WO2017/062605
PCT Pub. Date: Apr. 13, 2017

(65) Prior Publication Data
US 2018/0296698 A1    Oct. 18, 2018

Related U.S. Application Data

(60) Provisional application No. 62/237,771, filed on Oct. 6, 2015.

(51) Int. Cl.
*A61K 48/00* (2006.01)
*C12N 9/22* (2006.01)
*C12N 15/10* (2006.01)
*C07K 14/47* (2006.01)
*C12N 15/11* (2006.01)

(52) U.S. Cl.
CPC ........ *A61K 48/005* (2013.01); *C07K 14/4703* (2013.01); *C12N 9/22* (2013.01); *C12N 15/102* (2013.01); *C12N 15/11* (2013.01); *C12N 2310/20* (2017.05); *C12N 2800/80* (2013.01)

(58) Field of Classification Search
CPC .............. A61K 48/005; C07K 14/4703; C12N 2310/20; C12N 2800/80; C12N 9/22; C12N 15/102; C12N 15/11
USPC ........................................................ 424/93.2
See application file for complete search history.

(56) References Cited

U.S. PATENT DOCUMENTS

2015/0232836 A1 *   8/2015   Krieg ...................... A61P 43/00
                                                           514/44 A
2018/0344817 A1 *  12/2018   Smith .................. A61K 38/465

FOREIGN PATENT DOCUMENTS

| KR | 10-2017-0030729 A | 3/2017 | |
| WO | WO-9214840 A1 * | 9/1992 | .......... C12Q 1/6883 |
| WO | 1992/020825 A1 | 11/1992 | |
| WO | WO-9220825 A1 * | 11/1992 | .......... C12Q 1/6841 |
| WO | 2015/089351 A1 | 6/2015 | |
| WO | 2015/089354 A1 | 6/2015 | |
| WO | WO-2015089351 A * | 6/2015 | .......... C12Y 301/00 |
| WO | WO-2015089354 A1 * | 6/2015 | ............. C12N 15/86 |
| WO | WO-2015148863 A2 * | 10/2015 | .......... C12N 15/113 |
| WO | 2017/062983 A1 | 4/2017 | |

OTHER PUBLICATIONS

Garber et al. Eur. J. Hum. Genet. (2008) 16(6):666-672. (Year: 2008).*
Wu, X., et al., "Target specificity of the CRISPR-Cas9 system" Quant. Biol. (2014) 2(2):59-70.
Park, C.Y, et al., "Reversion of FMR1 Methylation and Silencing by Editing the Triplet Repeats in Fragile X iPSC-Derived Neurons" Cell Rep. (2015) 13(2):234-41.
Rodriguez, E., et al., "247. AAV-CRISPR: A New Therapeutic Approach To Nucleotide Repeat Diseases" Mol. Ther. (2014) 22(Supplement 1):S94.
Garber, K.B., et al., "Fragile X syndrome" Eur. J. Hum. Genet. (2008) 16(6):666-72.

* cited by examiner

*Primary Examiner* — Janet L Epps-Smith
(74) *Attorney, Agent, or Firm* — Robert C. Netter, Jr.; Dann, Dorfman, Herrell & Skillman

(57) ABSTRACT

Compositions and methods are provided for the inhibition, treatment and/or prevention of fragile X syndrome and related disorders.

Figure 2:
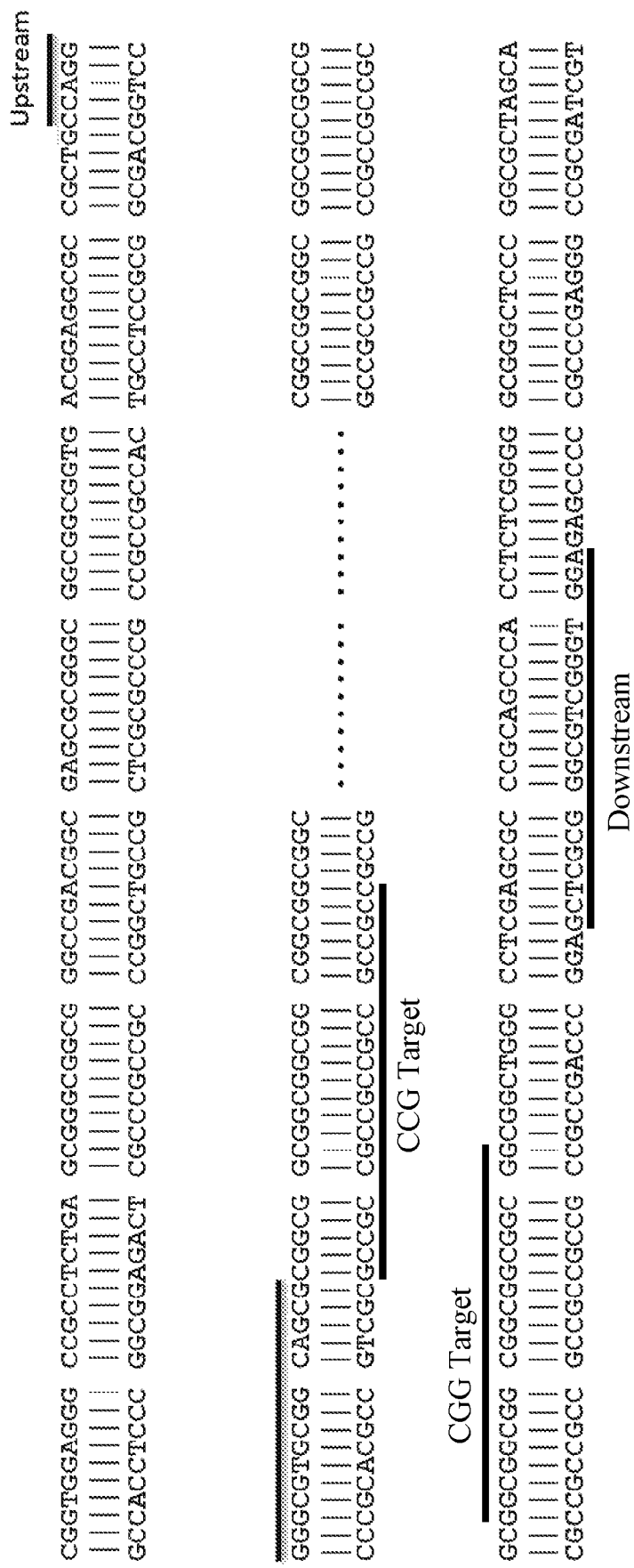

14 Claims, 13 Drawing Sheets
Specification includes a Sequence Listing.

ATGCATTTGATTTCCCACGCCACTGAGTGCACCTCTGCAGAAATGGGGTTCTGG
CCCTCGCGAGGCAGTGCGACCTGTCACCGCCCTTCAGCCTTCCGCCCTCCACCA
                              α-Pol/Nrf-1      Sp1
AGCCCGCCGGCACGCCCGCGTCTGTCTTTCGACCCGGCACCCCGGCCGGT
     AGB/EBP      Sp1
TCCCAGCAGGCGCGCATGCCGCGCCTCCCAGGCCACTTGAAGAGAGGGGGGC
              AP2
CGAGGGGCTGAGCCCGCGGGGGAGGGAACAGCGTTGATCACGTGACGTGTTTC
                                        CREB
AGTGTTTACACCCGCAGCCGGGGTTCGGCCCTCAGTCAGCGCTCAGCTCC
                                              *Zeste
GTTTCGGTTCACTTCCGGCTGAGGCCTCTGAGCGGGCGGGCGGGCGACGG
CGAGCGGGCGGAGCGGGCGGAGCCGGGCGCTGCCAGGCGGTGCGGCAGC
AGTGTTTACACCCGCAGCCGGGGTTCGGCCCTCAGTCAGCGCTCAGCTCC
CGGCGGGCGGGCGGGCGG·········CGGCGGGCGGGCGG
CGGCGGCTGGCCCTGAGCGGGCGGAGCCCACCTCTCGGGGCTCCCGGG
                              Exon 1
CTAGCAGGGTCGAAGAGAAGATGGAGGAGCTGGTGGTGAAGTGCGGGCTCCAA
TGGCGCTTTCTACAAGTACTTGGCTCTAGGCAGGCCCCATCTTCGCCCTTCCT
TCCTCCCTTTCTTCTTCTTGTCGGTGTCGGGGAGGCAGGCCCGGGGCCCTTCC

Figure 1

Figure 3

```
CGGTGGAGGG CCGCCTCTGA GCGGGGCGGC GGCCGACGGC GGCGGCGGTG GGCGGCGGGC ACGGAGGCGC CGCTGCCAGG
           |||||||||| |||||||||| |||||||||| |||||||||| |||||||||| |||||||||| |||||||||| ||||||||||
GCCACCTCCC GGCGGAGACT CGCCCCGCCG CCGGCTGCCG CCGCCGCCAC CCGCCGCCCG TGCCTCCGCG GCGACGGTCC

GGGCGTGCGG CAGCGCGGGG GCGGGGCGGG CGGCGGGCGG                     CGGGGCGGC        GGCGGGGCG
|||||||||| |||||||||| |||||||||| ||||||||||     . . . . .      ||||||||        |||||||||
CCCGCACGCC GTCGCGCCCC CGCCCCGCCC GCCGCCCGCC                     GCCCCGCCG        CCGCCCCGC
           CGG Boundary GCGGCGGCGG CGGCGGGCGG GGCGGCTGGG CCTCGAGCGC CCGCAGCCCA CCTCTCGGGG GCGGGCTCCC GGCGCTAGCA
|||||||||| |||||||||| |||||||||| |||||||||| |||||||||| |||||||||| |||||||||| ||||||||||
CGCCGCCGCC GCCGCCCGCC CCGCCGACCC GGAGCTCGCG GGCGTCAGGT GGAGAGCCCC CGCCCGAGGG CCGCGATCGT
                      CCG Boundary
```

Figure 3

Figure 12A

SEQUENCE LISTING

<160> NUMBER OF SEQ ID NOS: 24

<210> SEQ ID NO 1
<211> LENGTH: 704
<212> TYPE: DNA
<213> ORGANISM: Homo sapiens
<220> FEATURE:
<221> NAME/KEY: misc_feature
<222> LOCATION: (466)...(468)
<223> OTHER INFORMATION: nnn = absent or cgg repeat(s)

<400> SEQUENCE: 1

```
atgcatttga tttcccacgc cactgagtgc acctctgcag aaatgggcgt tctggccctc      60
gcgaggcagt gcgacctgtc accgcccttc agccttcccg ccctccacca agcccgcgca     120
cgcccggccc gcgcgtctgt ctttcgaccc ggcaccccgg ccggttccca gcagcgcgca     180
tgcgcgcgct cccaggccac ttgaagagag agggcggggc cgaggggctg agcccgcggg     240
gggagggaac agcgttgatc acgtgacgtg gtttcagtgt ttacacccgc agcgggccgg     300
gggttcggcc tcagtcaggc gctcagctcc gtttcggttt cacttccggt ggagggccgc     360
ctctgagcgg gcggcgggcc gacggcgagc gcgggcggcg gcggtgacgg aggcgccgct     420 gccaggggggc gtgcggcagc gcggcggcgg cggcggcggc ggcggnnncg gcggcggcgg     480
cggcggcggc ggctgggcct cgagcgcccg cagcccacct ctcgggggcg ggctcccggc     540
```

```
gctagcaggg ctgaagagaa gatggaggag ctggtggtgg aagtgcgggg ctccaatggc    600
gctttctaca aggtacttgg ctctagggca ggccccatct tcgcccttcc ttccctccct    660
tttcttcttg gtgtcggcgg gaggcaggcc cggggccctc ttcc                     704
```

```
<210> SEQ ID NO 2
<211> LENGTH: 236
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (141)...(143)
<223> OTHER INFORMATION: nnn = absent or cgg repeat(s)

<400> SEQUENCE: 2
gctccgtttc ggtttcactt ccggtggagg gccgcctctg agcgggcggc gggccgacgg     60
cgagcgcggg cggcggcggt gacggaggcg ccgctgccag gggcgtgcg gcagcgcggc    120 ggcggcggcg gcggcggcgg nnncggcggc ggcggcggcg gcggcggctg ggcctcgagc   180
gcccgcagcc cacctctcgg gggcgggctc ccggcgctag cagggctgaa gagaag       236
```

```
<210> SEQ ID NO 3
<211> LENGTH: 223
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (121)...(123)
<223> OTHER INFORMATION: nnn = absent or cgg repeat(s)

<400> SEQUENCE: 3
cggtggaggg ccgcctctga gcgggcggcg ggccgacggc gagcgcgggc ggcggcggtg     60
acggaggcgc cgctgccagg gggcgtgcgg cagcgcggcg gcggcggcgg cggcggcggc   120
nnncggcggc ggcggcggcg gcggcggcgg cggcggcggc ggcggcggct gggcctcgag   180
cgcccgcagc ccacctctcg ggggcgggct cccggcgcta gca                     223
```

```
<210> SEQ ID NO 4
<211> LENGTH: 240
<212> TYPE: DNA
<213> ORGANISM: Artificial Sequence
<220> FEATURE:
<223> OTHER INFORMATION: Synthetic Sequence

<400> SEQUENCE: 4
cggtggaggg ccgcctctga gcgggcggcg ggccgacggc gagcgcgggc ggcggcggtg     60
acggaggcgc cgctgccagg gggcgtgcgg cagcgcggcg gcggcggcgg cggcggcggc   120
ggaggcggcg gcggcggcgg cggcggcggc ggaggcggcg gcggcggcgg cggcggcggc   180
ggcggctggg cctcgagcgc ccgcagccca cctctcgggg gcgggctccc ggcgctagca   240
```

```
<210> SEQ ID NO 5
<211> LENGTH: 20
<212> TYPE: DNA
<213> ORGANISM: Artificial Sequence
<220> FEATURE:
<223> OTHER INFORMATION: Target Sequence

<400> SEQUENCE: 5
```

```
ccaggggcg tgcggcagcg                                               20

<210> SEQ ID NO 6
<211> LENGTH: 18
<212> TYPE: DNA
<213> ORGANISM: Artificial Sequence
<220> FEATURE:
<223> OTHER INFORMATION: Target Sequence

<400> SEQUENCE: 6
gcagcgcggc ggcggcgg                                                18

<210> SEQ ID NO 7
<211> LENGTH: 20
<212> TYPE: DNA
<213> ORGANISM: Artificial Sequence
<220> FEATURE:
<223> OTHER INFORMATION: Target Sequence

<400> SEQUENCE: 7
aggtgggctg cgggcgctcg                                              20

<210> SEQ ID NO 8
<211> LENGTH: 225
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (158)...(160)
<223> OTHER INFORMATION: nnn = cgg repeat(s)

<400> SEQUENCE: 8
gctcagctcc gtttcggttt cacttccggt ggagggccgc ctctgagcgg gcggcgggcc    60
gacggcgagc gcgggcggcg gcggtgacgg aggcgccgct gccaggggc gtgcggcagc   120 gcggcggcgg cggcggcggc ggcggcggag gcggcggnnn cggcggcggc ggcggctggg   180
cctcgagcgc ccgcagccca cctctcgggg gcgggctccc ggcgc                   225

<210> SEQ ID NO 9
<211> LENGTH: 224
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (122)...(124)
<223> OTHER INFORMATION: nnn = cgg repeats

<400> SEQUENCE: 9
gctcagctcc gtttcggttt cacttccggt ggagggccgc ctctgagcgg gcggcgggcc    60
gacggcgagc gcgggcggcg gcggtgacgg aggcgccgct gccaggggc gtgcggcagc   120 gnnnctgggc ctcgagcgcc cgcagcccac ctctcggggg cgggctcccg gcgctagcag   180
ggctgaagag aagatggagg agctggtggt ggaagtgcgg ggct                    224

<210> SEQ ID NO 10
<211> LENGTH: 80
<212> TYPE: RNA
<213> ORGANISM: Artificial Sequence
<220> FEATURE:
<223> OTHER INFORMATION: scaffold gRNA

<400> SEQUENCE: 10
```

```
guuuuagagc uagaaauagc aaguuaaaau aaggcuaguc cguuaucaac uugaaaaagu    60
ggcaccgagu cggugcuuuu                                                80

<210> SEQ ID NO 11
<211> LENGTH: 30
<212> TYPE: DNA
<213> ORGANISM: Artificial Sequence
<220> FEATURE:
<223> OTHER INFORMATION: forward primer

<400> SEQUENCE: 11
gctcagctcc gtttcggttt cacttccggt                                     30

<210> SEQ ID NO 12
<211> LENGTH: 30
<212> TYPE: DNA
<213> ORGANISM: Artificial Sequence
<220> FEATURE:
<223> OTHER INFORMATION: reverse primer

<400> SEQUENCE: 12
agccccgcac ttccaccacc agctcctcca                                     30

<210> SEQ ID NO 13
<211> LENGTH: 20
<212> TYPE: DNA
<213> ORGANISM: Artificial Sequence
<220> FEATURE:
<223> OTHER INFORMATION: target sequence

<400> SEQUENCE: 13
tgacggaggc gccgctgcca                                                20

<210> SEQ ID NO 14
<211> LENGTH: 18
<212> TYPE: RNA
<213> ORGANISM: Artificial Sequence
<220> FEATURE:
<223> OTHER INFORMATION: gRNA sequence

<400> SEQUENCE: 14
gcagcgcggc ggcggcgg                                                  18

<210> SEQ ID NO 15
<211> LENGTH: 20
<212> TYPE: RNA
<213> ORGANISM: Artificial Sequence
<220> FEATURE:
<223> OTHER INFORMATION: gRNA sequence

<400> SEQUENCE: 15 agugggcug cgggcgcucg                                                 20

<210> SEQ ID NO 16
<211> LENGTH: 20
<212> TYPE: RNA
<213> ORGANISM: Artificial Sequence
<220> FEATURE:
<223> OTHER INFORMATION: gRNA sequence

<400> SEQUENCE: 16 ccaggggcg ugcggcagcg                                                 20

<210> SEQ ID NO 17
```

```
<211> LENGTH: 21
<212> TYPE: DNA
<213> ORGANISM: Artificial Sequence
<220> FEATURE:
<223> OTHER INFORMATION: Target sequence

<400> SEQUENCE: 17
ccgccgccgc cgccgccgcc g                                              21

<210> SEQ ID NO 18
<211> LENGTH: 20
<212> TYPE: DNA
<213> ORGANISM: Artificial Sequence
<220> FEATURE:
<223> OTHER INFORMATION: Target sequence

<400> SEQUENCE: 18
ggcggcggcg gcggcggcgg                                                20

<210> SEQ ID NO 19
<211> LENGTH: 22
<212> TYPE: DNA
<213> ORGANISM: Artificial Sequence
<220> FEATURE:
<223> OTHER INFORMATION: Target sequence

<400> SEQUENCE: 19
ggcagcgcgg cggcggcggc gg                                             22

<210> SEQ ID NO 20
<211> LENGTH: 19
<212> TYPE: DNA
<213> ORGANISM: Artificial Sequence
<220> FEATURE:
<223> OTHER INFORMATION: Target sequence

<400> SEQUENCE: 20
ggcccagccg ccgccgccg                                                 19

<210> SEQ ID NO 21
<211> LENGTH: 21
<212> TYPE: RNA
<213> ORGANISM: Artificial Sequence
<220> FEATURE:
<223> OTHER INFORMATION: gRNA sequence

<400> SEQUENCE: 21
ccgccgccgc cgccgccgcc g                                              21

<210> SEQ ID NO 22
<211> LENGTH: 20
<212> TYPE: RNA
<213> ORGANISM: Artificial Sequence
<220> FEATURE:
<223> OTHER INFORMATION: gRNA sequence

<400> SEQUENCE: 22
ggcggcggcg gcggcggcgg                                                20

<210> SEQ ID NO 23
<211> LENGTH: 22
<212> TYPE: RNA
<213> ORGANISM: Artificial Sequence
<220> FEATURE:
<223> OTHER INFORMATION: gRNA sequence

<400> SEQUENCE: 23
```

```
ggcagcgcgg cggcggcggc gg                                                    22
```

```
<210> SEQ ID NO 24
<211> LENGTH: 19
<212> TYPE: RNA
<213> ORGANISM: Artificial Sequence
<220> FEATURE:
<223> OTHER INFORMATION: gRNA sequence

<400> SEQUENCE: 24
```

```
ggcccagccg ccgccgccg                                                        19
```

COMPOSITIONS AND METHODS FOR TREATING FRAGILE X SYNDROME AND RELATED SYNDROMES This application is a § 371 application of PCT/US2016/055723, filed Oct. 6, 2016, which claims priority under 35 U.S.C. § 119(e) to U.S. Provisional Patent Application No. 62/237,771, filed Oct. 6, 2015. The foregoing applications are incorporated by reference herein.

FIELD OF THE INVENTION

The present invention relates to fragile X syndrome and related disorders. Specifically, the instant invention provides compositions and methods for the treatment and/or prevention of fragile X syndrome and related disorders.

BACKGROUND OF THE INVENTION

The Fragile X Mental Retardation 1 (FMR1) gene has a CGG trinucleotide repeat in the 5' untranslated region of the gene. The normal length of this locus is between 5 and 44 CGG repeats. However, longer stretches of CGG repeats are prone to instability when inherited from parent to child. A premutation allele (55-200 CGG repeats) is the causative mutation of Fragile X-associated Tremor/Ataxia Syndrome (FXTAS), a late-onset neurodegenerative disorder, and Fragile X-associated Primary Ovarian Insufficiency (FX-POI), a condition that results in fertility issues in females. A full mutation (greater than 200 CGG repeats) is the predominant cause of fragile X syndrome (FXS). FXS is the most common single gene cause of intellectual disability and autism spectrum disorders. Individuals with a FMR1 premutation are at risk of developing FXTAS or FXPOI (1:130-1:256 females and 1:250-1:810 males) and individuals with a full mutation and are diagnosed with FXS (1:2500 to 1:8000 females; 1:5000 males).

When a premutation allele is present on the FMR1 gene, it is transcribed into the messenger RNA (mRNA). However, it is upstream of the start codon and will not be translated as part of the canonical protein isoforms. While the mechanisms resulting in FXTAS and FXPOI are not fully understood, the longer CGG repeat stretch is thought to alter how the gene is expressed (higher mRNA levels, and alternative translation initiation) and how other proteins interact with the CGG repeat or alternative FMRP isoform. Alternatively, when a full mutation allele is present on the FMR1 gene, it undergoes epigenetic changes including methylation of the cytosine nucleotides within the CGG repeat and along the promoter region, and modification of histones to have a heterochromatin signature. These changes result in FMR1 silencing, such that the gene is neither significantly transcribed into mRNA nor significantly translated into protein.

There is a need for effective therapeutics for treating fragile X syndrome and related disorders.

SUMMARY OF THE INVENTION

In accordance with one aspect of the instant invention, methods and compositions for inhibiting, treating, and/or preventing fragile X syndrome and related disorders (e.g., Fragile X-associated Tremor/Ataxia Syndrome (FXTAS) or Fragile X-associated Primary Ovarian Insufficiency (FX-POI)) in a subject are provided. In accordance with another aspect of the instant invention, methods (e.g., in vitro methods) for reducing the number of CGG repeats in the 5' untranslated region of the FMR1 gene in a cell and/or reactivating the silenced FMR1 gene (i.e., increasing expression of the FMR1 gene) are provided. In a particular embodiment, the methods of the instant invention comprise administering to the subject or cell a nucleic acid molecule encoding Cas9 and at least one guide RNA, wherein the guide RNA targets a sequence in the 5' untranslated region of the FMR1 gene. The methods of the instant invention may further comprise administering at least one donor DNA to the subject or cell. The methods of the instant invention may further comprise administering a nucleic acid molecule (e.g., an expression vector or viral vector) encoding a fusion protein comprising an inactive Cas9 and a transcription activator peptide or protein to the subject or cell (optionally with a guide RNA). In a particular embodiment, the guide RNA are administered to the subject or cell as a nucleic acid molecule (e.g., an expression vector or viral vector) encoding the guide RNA. In a particular embodiment, the methods of the instant invention comprise administering two guide RNAs to the subject or cell, wherein the guide RNAs target a sequence within SEQ ID NO: 2 (inclusive of its complement). In a particular embodiment, one guide RNA targets a sequence 5' of or at least partly within the CGG repeat region and one guide RNA targets a sequence 3' of the CGG repeat region. In a particular embodiment, at least one of the guide RNAs targets a sequence specifically set forth herein.

The instant invention also encompasses guide RNAs, nucleic acid molecules (e.g., an expression vector or viral vector) encoding the guide RNAs, and compositions comprising the guide RNAs and/or nucleic acid molecules (e.g., an expression vector or viral vector) encoding the guide RNAs. In a particular embodiment, the composition and nucleic acid molecules (e.g., an expression vector or viral vector) encoding the guide RNAs contain or encode more than one guide RNA.

BRIEF DESCRIPTIONS OF THE DRAWING

FIG. 1 provides a partial DNA sequence of FMR1 and its 5' untranslated region (SEQ ID NO: 1). The underlined region (SEQ ID NO: 2), which is downstream of the promoter and upstream of the coding sequence, is targetable using CRISPR/Cas9.

FIG. 2 provides examples of designed gRNAs targeting the FMR1 trinucleotide repeat. Depicted FMR1 sequence is SEQ ID NO: 3. The bars correspond to the gRNA sequences. The Upstream gRNA target sequence is CCA GGG GGC GTG CGG CAG CG (SEQ ID NO: 5), the Downstream gRNA target sequence is AGG TGG GCT GCG GGC GCT CG (SEQ ID NO: 7), the CCG Target gRNA target sequence is CCG CCG CCG CCG CCG CCG CCG (SEQ ID NO: 17), and the CGG Target gRNA target sequence is GGC GGC GGC GGC GGC GG (SEQ ID NO: 18).

FIG. 3 provides designed gRNAs targeting the boundary region of the FMR1 trinucleotide repeat. Depicted FMR1 sequence is SEQ ID NO: 3. The bars correspond to the gRNA sequences. The CGG Boundary gRNA target sequence is G GCA GCG CGG CGG CGG CGG CGG (SEQ ID NO: 19) and the CCG Boundary gRNA target sequence is GGC CCA GCC GCC GCC GCC G (SEQ ID NO: 20).

Figure 4:
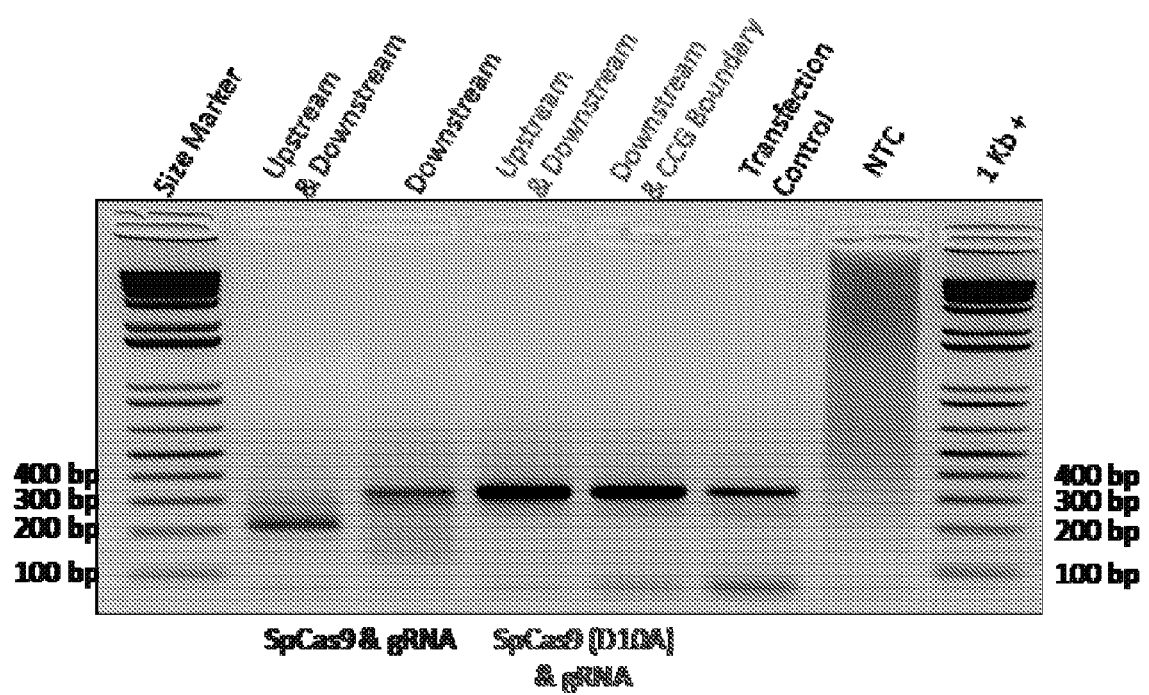

FIG. 4 provides data showing the deletion of the FMR1 trinucleotide repeat in HEK 293 cells with the indicated gRNAs and SpCas9 or SpCas9 (D10A).

Figure 5:
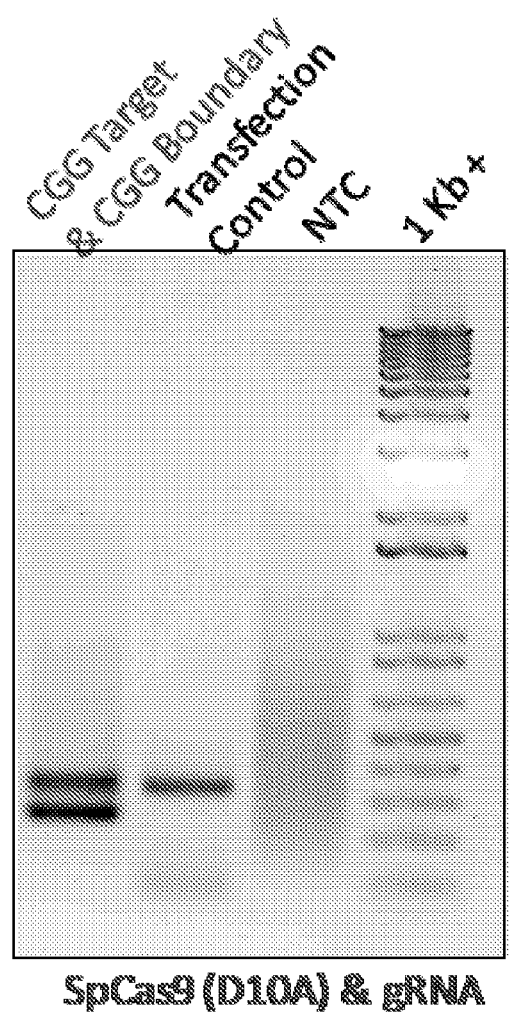

FIG. 5 provides data showing deletion of the FMR1 trinucleotide repeat in HEK 293 cells using SpCas9 (D10A).

Figure 6:
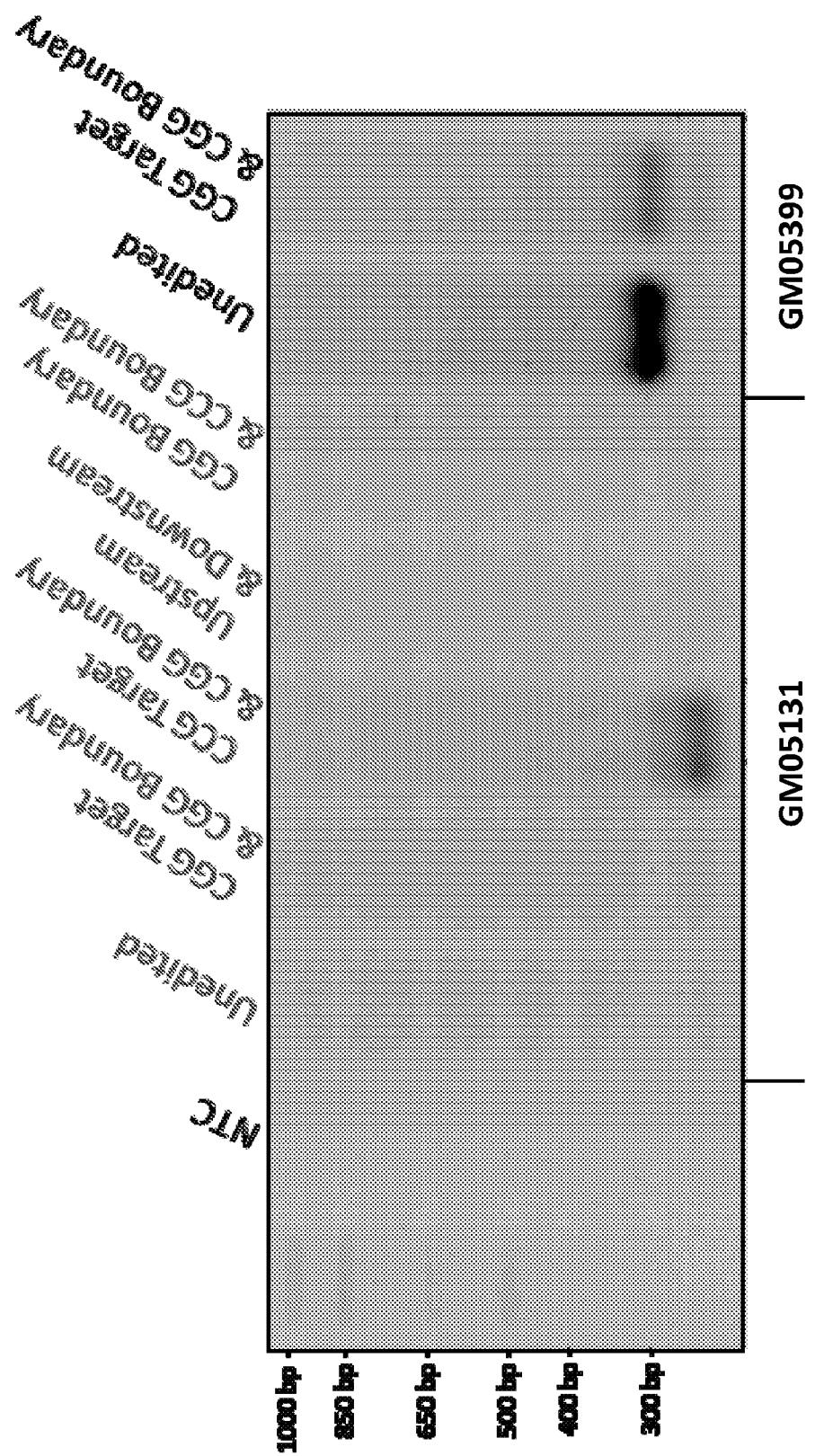

FIG. 6 provides data showing deletion of the FMR1 trinucleotide repeat in human fibroblasts. GM05131 fibroblasts harbor a full mutation and GM05399 fibroblasts have a normal CGG repeat size.

Figure 7:
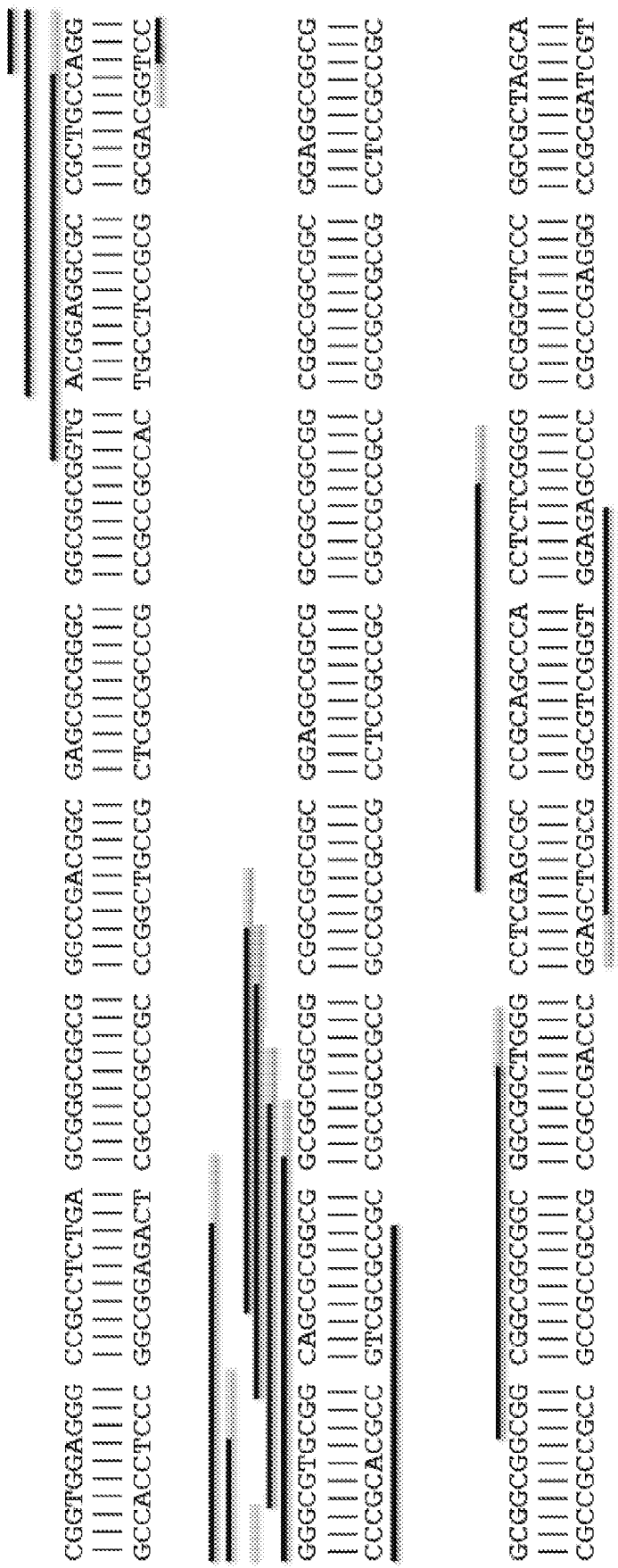

FIG. 7 provides gRNA sequences to target the FMR1 trinucleotide repeat. Depicted FMR1 sequence is SEQ ID NO: 4. The black bars correspond to the gRNA sequences and the grey bars correspond to the adjacent PAM sequences downstream of the target sequence.

Figure 8:
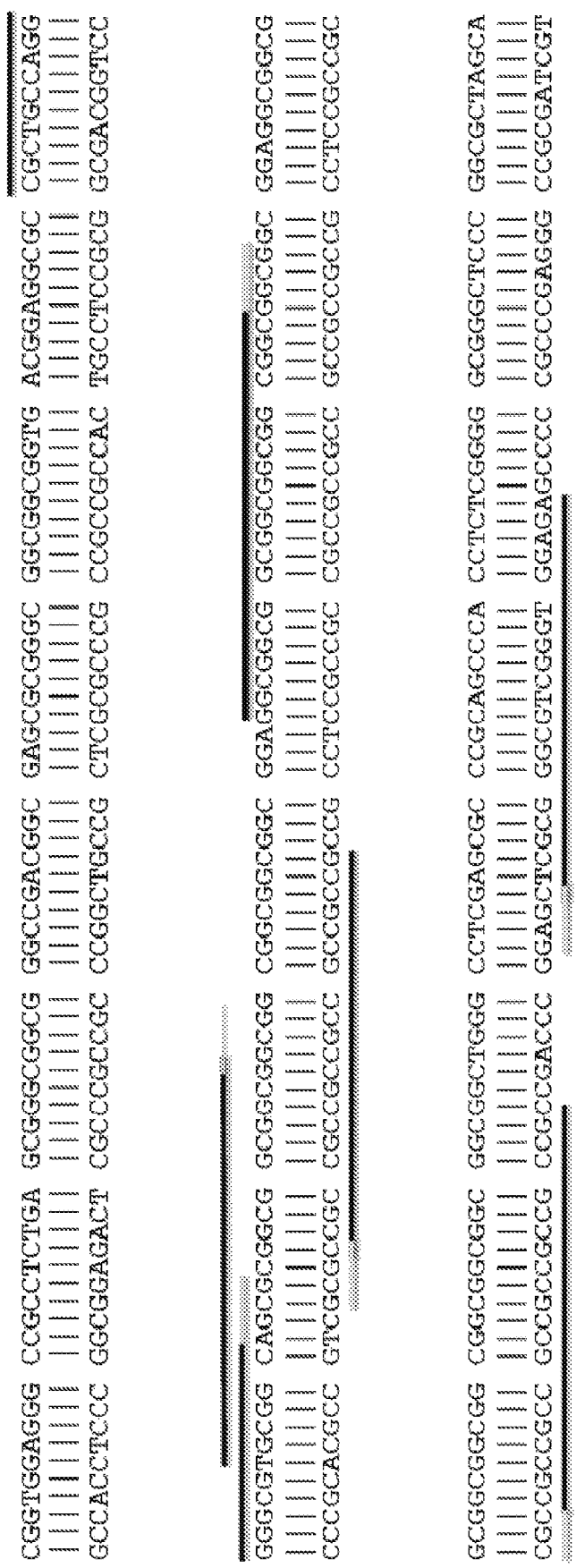

FIG. 8 provides gRNA sequences to target the FMR1 trinucleotide repeat using engineered SpCas9. Depicted FMR1 sequence is SEQ ID NO: 4. The black bars correspond to the gRNA sequences and the grey bars correspond to the adjacent PAM sequences downstream of the target sequence.

Figure 9:
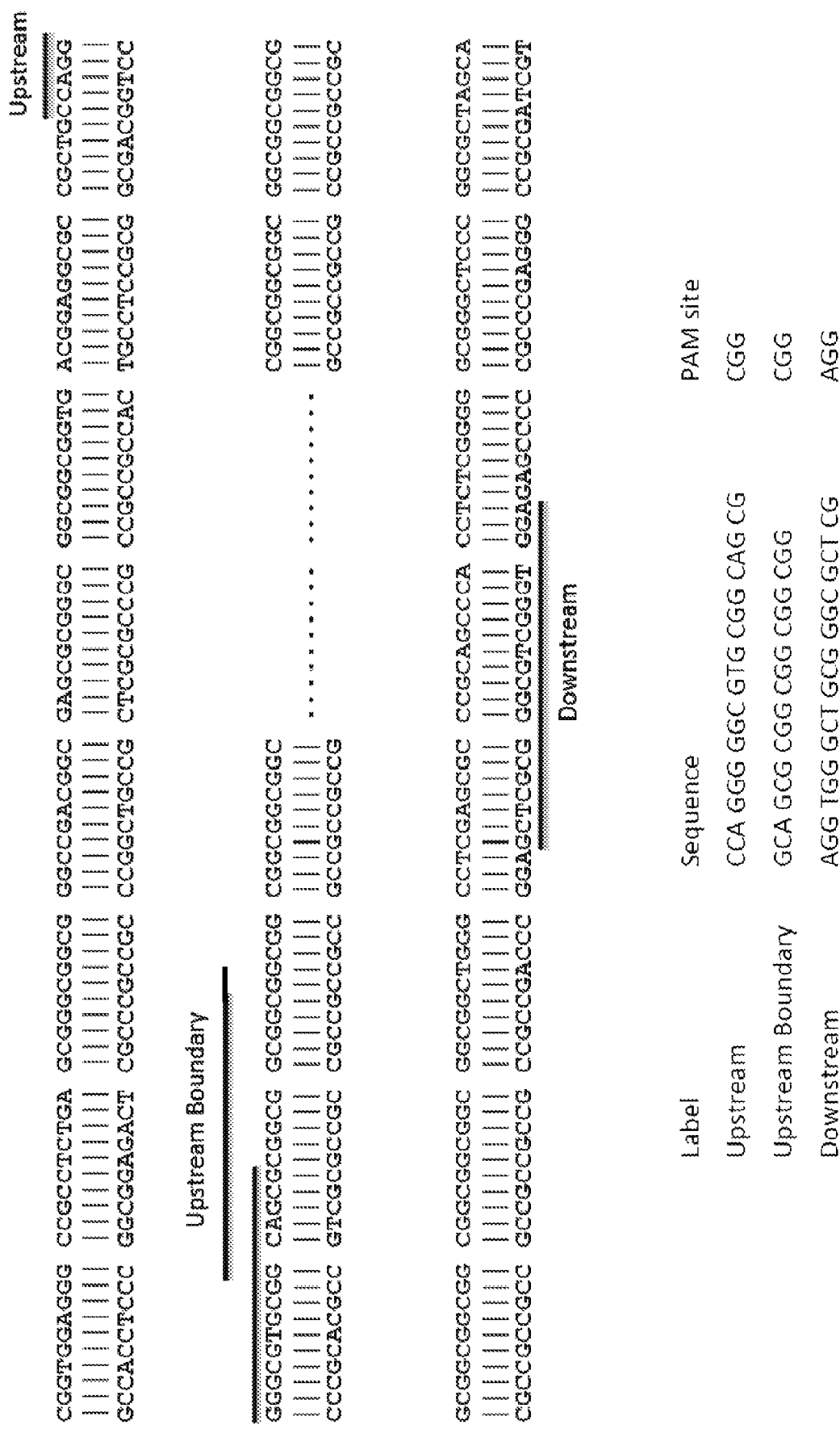

FIG. 9 provides examples of designed gRNAs targeting the FMR1 trinucleotide repeat. Depicted FMR1 sequence is SEQ ID NO: 3. The bars correspond to the gRNA sequences. Sequences corresponding to the gRNA that complements the target sequence of the FMR1 gene are provided. Upstream sequence: SEQ ID NO: 5; Upstream Boundary sequence: SEQ ID NO: 6; and Downstream sequence: SEQ ID NO: 7.

Figure 10:
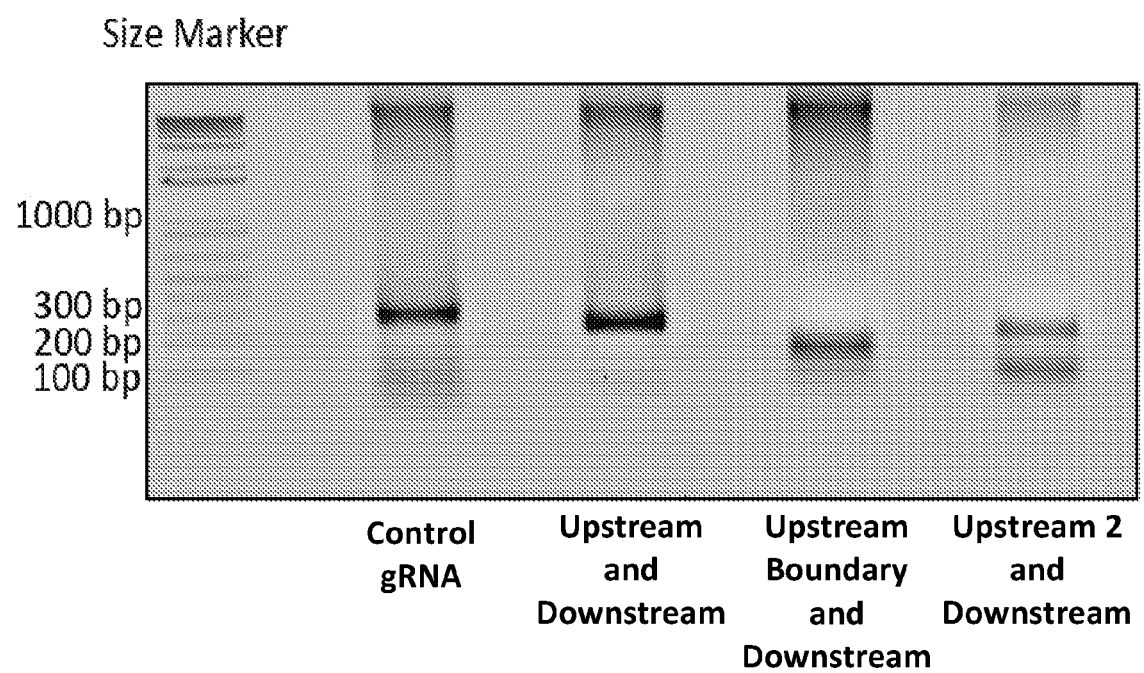

FIG. 10 provides data showing the deletion of the FMR1 trinucleotide repeat in HEK 293 cells with the indicated gRNAs and SpCas9.

Figure 11A:
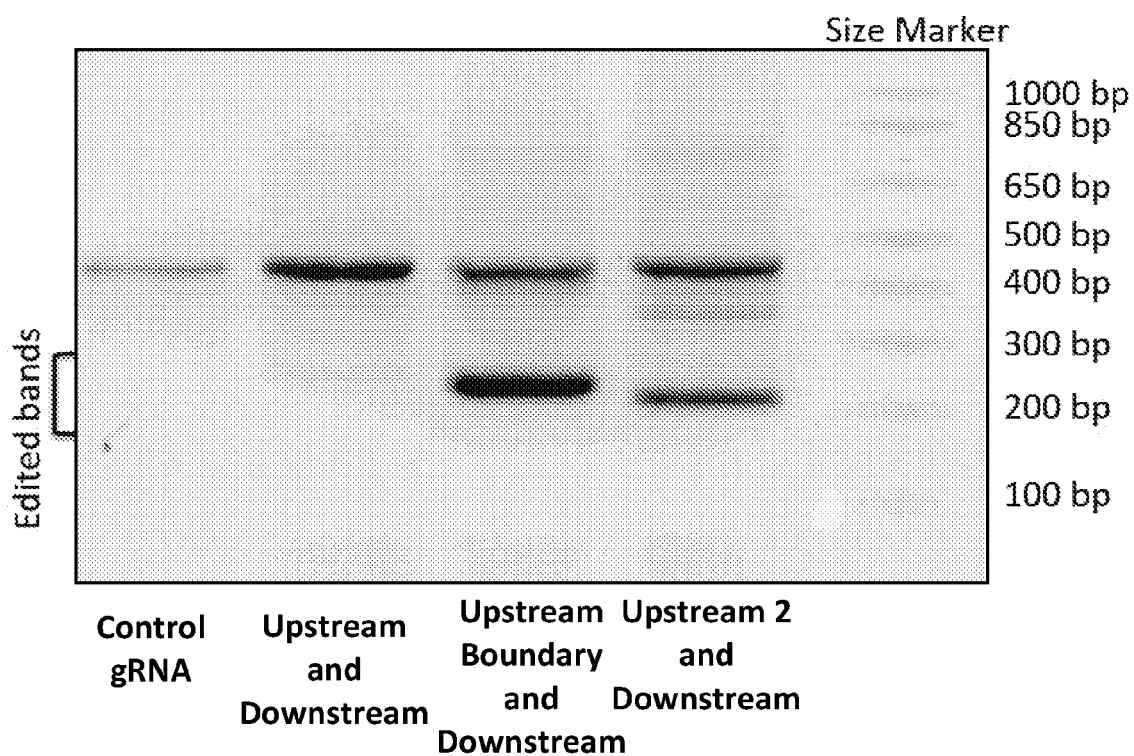
Figure 11B:
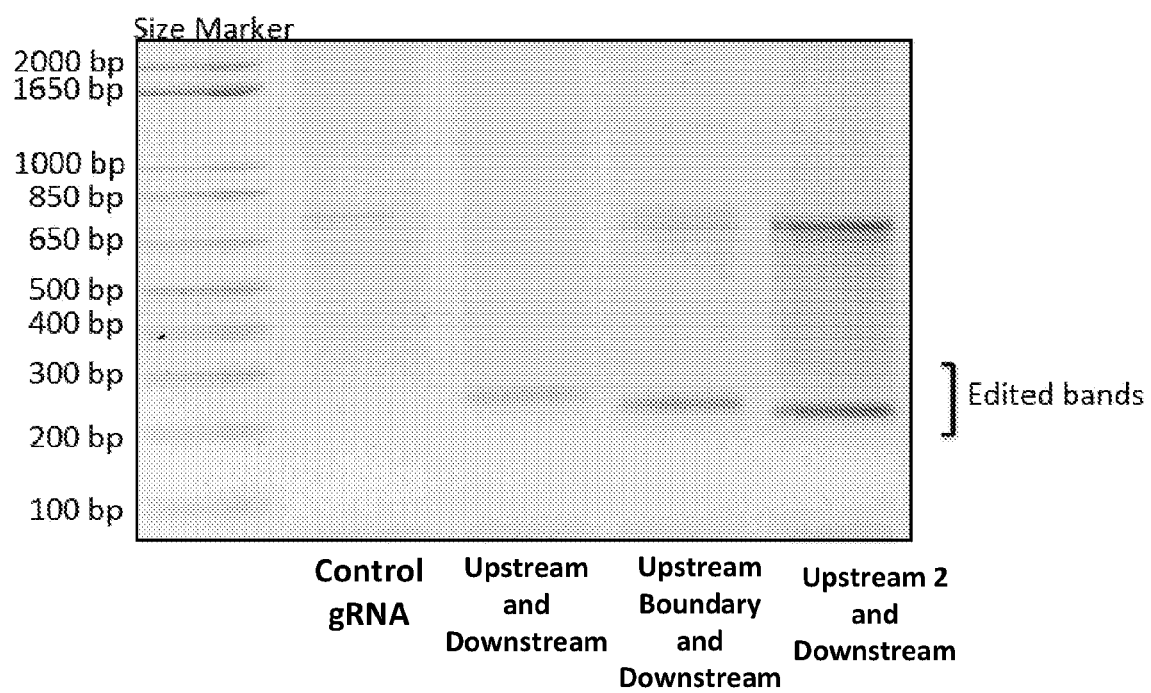

FIG. 11A provides data showing the deletion of the FMR1 trinucleotide repeat in human fibroblasts with a premutation with the indicated gRNAs. FIG. 11B provides data showing the deletion of the FMR1 trinucleotide repeat in human fibroblasts with a full mutation with the indicated gRNAs.

Figure 12A:
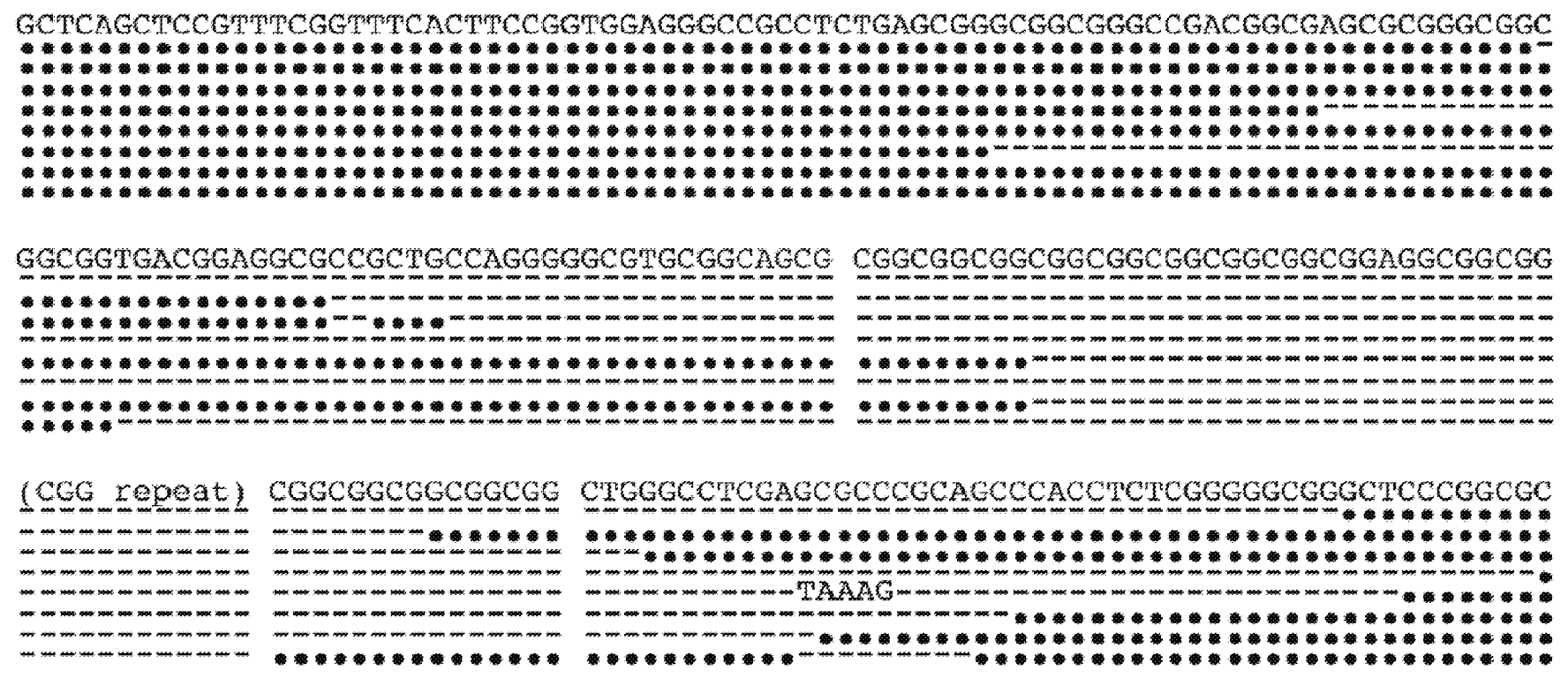
Figure 12B:
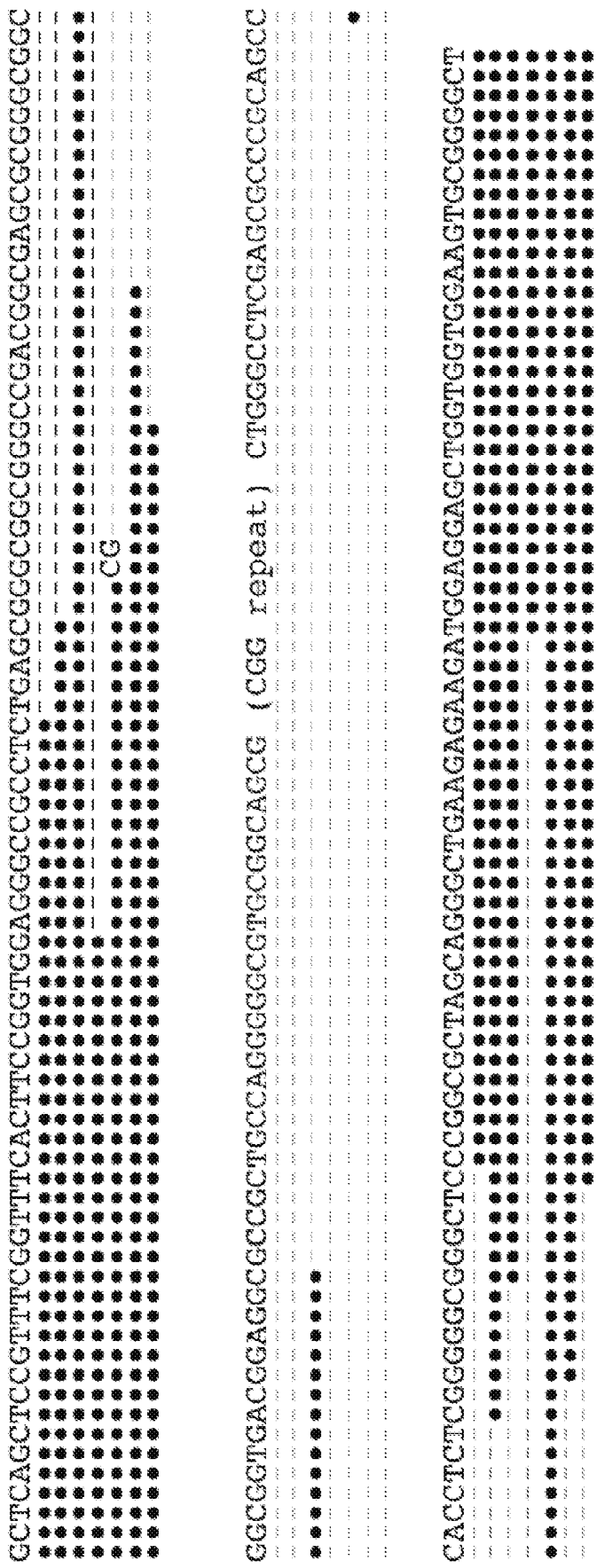

FIG. 12A provides sequences of the CGG repeat locus after deletion in HEK 293 cells with the Upstream Boundary gRNA and Downstream gRNA. Shown sequence is SEQ ID NO: 8. FIG. 12B provides sequences of the CGG repeat locus after deletion in HEK 293 cells with the Upstream gRNA and Downstream gRNA. Shown sequence is SEQ ID NO: 9.

DETAILED DESCRIPTION OF THE INVENTION

Herein, therapeutics are described which modify a DNA sequence in the Fragile X Mental Retardation 1 (FMR1) gene in a way that reduces, or eliminates, the pathological effects of a mutation. The mutation being targeted—e.g., by gene therapy—is a CGG trinucleotide repeat in the 5' untranslated region of the gene. In a particular embodiment, the methods of the instant invention comprise correcting the FMR1 mutation on the DNA level by utilizing Clustered Regularly Interspaced Short Palindromic Repeats (CRISPR)/Cas9 technology. CRISPR is a biological defense system in which Cas9 (a DNA nuclease) is able to cause a break on a precise DNA sequence by using a short RNA sequence as a guide, resulting in a small insertion or deletion. Multiple CRISPR induced breaks in the same region can result in a larger deletion. Herein, a number of guide RNAs (gRNAs) have been designed to target the FMR1 CGG repeats and the adjacent sequences in order to induce a deletion of some or all of the CGG repeats. gRNA combinations may be employed to achieve the desired deletions. Additionally, modified or unmodified (e.g., wild type) Cas9 may be used to balance editing efficiency with off target effects.

As described herein below, Cas9 and gRNA encoding DNA were introduced into human embryonic kidney cells (HEK293 cell line) with a normal CGG repeat length and the CGG repeat locus was evaluated. Several of the gRNA combinations produced deletions within or encompassing the CGG repeat. The gRNAs were also evaluated in human fibroblast cell lines that harbor either a premutation or a full mutation allele.

In a particular embodiment, the CRISPR/Cas9 approach is also used to reactivate the silenced FMR1 gene following editing of the CGG repeat locus. In a particular embodiment, a Cas9 (e.g., an inactive Cas9) may be tethered or linked to (e.g., to form a fusion protein) a protein or peptide that can activate gene expression (e.g., a transcription activator peptide or a transcription factor (e.g., VP64-p65-Rta (VPR), VP64, p300, or p300 core)) so that the activator will be near the FMR1 promoter while Cas9 complexes with the targeted sequence (see, e.g., Perez-Pinera et al. (2013) Nature Methods 10:973-976; www.addgene.org/47107; www.addgene.org/crispr/activate/). A nucleic acid molecule encoding the activator Cas9 can be administered simultaneously and/or after editing the CGG repeat. A guide RNA or nucleic acid encoding the guide RNA may also be co-administered with the activator Cas9. The guide RNA may be the same or different than the one employed for editing the CGG repeat. The gRNAs may be designed for the activator Cas9 to take into account new sequences being made with the repair of the deleted CGG repeats.

Clustered, regularly interspaced, short palindromic repeat (CRISPR)/Cas9 technology is well known in the art (see, e.g., Sander et al. (2014) Nature Biotech., 32:347-355; Jinek et al. (2012) Science, 337:816-821). Cas9 possesses two nuclease domains, a RuvC-like nuclease domain and a HNH-like nuclease domain, and is responsible for the destruction of the target DNA (Jinek et al. (2012) Science, 337:816-821; Sapranauskas et al. (2011) Nucleic Acids Res. 39:9275-9282). The two nucleases generate double-stranded breaks. The double-stranded endonuclease activity of Cas9 requires a target sequence (~20 nucleotides) and a short conserved sequence (~2-5 nts) known as protospacer-associated motif (PAM), which follows immediately 3'-of the CRISPR RNA (crRNA) complementary sequence (Jinek et al. (2012) Science, 337:816-821; Nishimasu et al. (2014) Cell 156(5):935-49; Swarts et al. (2012) PLoS One, 7:e35888; Sternberg et al. (2014) Nature 507(7490):62-7). Guidelines and computer-assisted methods for generating gRNAs are available (see, e.g, CRISPR Design Tool (crispr.mit.edu/); Hsu et al. (2013) Nat. Biotechnol. 31:827-832; www.addgene.org/CRISPR, and CRISPR gRNA Design tool—DNA2.0 (www.dna20.com/eCommerce/startCas9)). Typically, the PAM sequence is present adjacent to the DNA target sequence but not in the gRNA sequence.

The binding specificity of the CRISPR/Cas9 complex depends on two different elements. First, the binding complementarity between the targeted genetic DNA (genDNA) sequence and the complementary recognition sequence of the gRNA. Second, the presence of a protospacer-adjacent motif (PAM) juxtaposed to the genDNA/gRNA complementary region. Whereas single point mutations in the complementary recognition sequence permit Cas9-mediated DNA cleavage, the preservation of an intact PAM motif is critical (Jinek et al. (2012) Science 337:816-821; Hsu et al. (2013) Nat. Biotech., 31:827-832; Sternberg et al. (2014) Nature 507:62-67). The PAM motif for *S. Pyogenes* Cas9 has been fully characterized, and is NGG or NAG (Jinek et al. (2012) Science 337:816-821; Hsu et al. (2013) Nat. Biotech., 31:827-832). While any nucleotide type can be found at the first position of the PAM motif, a C/T nucleotide at position 2 and/or a C/T/A nucleotide at position 3 can disrupt the PAM motif and subsequently inhibit Cas9-mediated dsDNA cleavage. Thus, PAM motifs containing single nucleotide polymorphisms (SNP) at positions two or three will confer allele cleavage selectivity when targeted with CRISPR/Cas9 complexes.

Gene editing based on bacterial endonucleases such as CRISPR-associated protein-9 (Cas9) from *Streptococcus pyogenes* has been described (Cong et al. (2013) Science 339:819-823; Ran et al. (2013) Nature Protocols 8:2281-2308; Mali et al. (2013) Science 339:823-826; Jinek et al. (2012) Science 337:816-821). The RNA-guided CRISPR/Cas9 system involves expressing Cas9 along with a gRNA such as a single guide RNA molecule (sgRNA). When coexpressed, gRNAs bind and recruit Cas9 to a specific genomic target sequence where it mediates a double strand DNA (dsDNA) break and activates the dsDNA break repair machinery. Specific DNA fragments can be deleted when two gRNA/Cas9 complexes generate dsDNA breaks at relative proximity. The double strand break can be repaired by non-homologous end joining (NHEJ) pathway yielding an insertion and/or deletion or, in the presence of a donor template, by homology-directed repair (HDR) pathway for replacement mutations (Overballe-Petersen et al. (2013) Proc. Natl. Acad. Sci. U.S.A. 110:19860-19865; Gong et al. (2005) Nat. Struct. Mol. Biol. 12:304-312). A Cas9 mutant may also be used in the instant invention (e.g., a mutant with an inactivated HNH and/or RuvC nuclease). In a particular embodiment, the mutant is Cas9 D10A. Cas9 D10A nicks single-strand DNA rather than generate a double strand break (Cong et al. (2013) Science, 339:819-823; Davis et al. (2014) Proc. Natl. Acad. Sci. USA, 111:E924-932). The nicks are repaired by HDR pathway. Two gRNAs can be used to generate a staggered double strand break with Cas9 D10A. Examples of Cas9 that can be used in the instant invention include, without limitation, *Streptococcus pyogenes* Cas9, Cas9 D10A, high fidelity Cas9 (Kleinstiver et al. (2016) Nature, 529:490-495; Slaymaker et al. (2016) Science, 351:84-88), Cas9 nickase (Ran et al. (2013) Cell, 154:1380-1389), *Streptococcus pyogenes* Cas9 with altered PAM specificities (e.g., SpCas9 VQR (NGAN or NGNG), SpCas9_EQR (NGAG), and SpCas9_VRER (NGCG); Kleinstiver et al. (2015) Nature, 523:481-485), *Staphylococcus aureus* Cas9 (NNGRRT, NNGRR), the CRISPR/Cpf1 system of *Acidaminococcus* (TTTN), and the CRISPR/Cpf1 system of Lachnospiraceae. In a particular embodiment, the Cas9 is SpCas9 or SpCas9 D10A. Notably, for those Cas9 with different PAM than SpCas9 or SpCas9 D10A, the guide RNA should be designed to be adjacent to the PAM of the Cas9 being used.

In accordance with the instant invention, methods of treating, inhibiting, and/or preventing fragile X syndrome and related disorders (e.g., FXPOI, FXTAS, etc.) are provided. In accordance with another aspect of the instant invention, methods (e.g., in vitro methods) for reducing the number of CGG repeats in the 5' untranslated region of the FMR1 gene in a cell and/or reactivating the silenced FMR1 gene (i.e., increasing expression of the FMR1 gene) are provided. In a particular embodiment, the methods of the instant invention comprise reducing the number of CGG repeats in the 5' untranslated region of the FMR1 gene. In a particular embodiment, the number of CGG repeats in the 5' untranslated region of the FMR1 gene is reduced to below 55 repeats, particularly below 45 repeats. In a particular embodiment, the method comprises reducing the number of CGG repeats using CRISPR/Cas9 technology. In a particular embodiment, the method comprises administering at least one Cas9 (e.g., a nucleic acid molecule encoding Cas9) and at least one gRNA (e.g., a nucleic acid molecule encoding said gRNA) to the cell or subject. The gRNA may target upstream (e.g., within about 100 bases of the CGG repeats) of the CGG repeats, downstream (e.g., within about 100 bases of the CGG repeats) of the CGG repeats, at the boundaries of the CGG repeats, and/or within the CGG repeats. In a particular embodiment, the gRNA targets the untranslated region of the FMR1 gene between the promoter and the CGG repeat domain (see, e.g., FIG. 1 and SEQ ID NO: 2). In a particular embodiment, the gRNA targets the untranslated region of the FMR1 gene between the CGG repeat domain and exon 1 (see, e.g., FIG. 1 and SEQ ID NO: 2). In a particular embodiment, a gRNA targeting the untranslated region of the FMR1 gene between the promoter and the CGG repeat domain and a gRNA targeting the untranslated region of the FMR1 gene between the CGG repeat domain and exon 1, are used). In a particular embodiment, one guide RNA targets a sequence 5' of or at least partly within the CGG repeat region and one guide RNA targets a sequence 3' of or at least partly within the CGG repeat region.

In a particular embodiment, the method further comprises the administration of a donor nucleic acid molecule (e.g., DNA). The donor DNA may be incorporated into the genetic DNA between the cleavage sites generated (e.g., by NHEJ). The donor DNA may be a replacement sequence of CGG repeats (e.g., from 5 to 54 repeats, particularly from 5 to 44 repeats), optionally comprising regions 5' and 3' of the CGG repeats from the 5' untranslated region of FMR1.

The nucleic acids of the instant invention may be administered consecutively (before or after) and/or at the same time (concurrently). The nucleic acid molecules may be administered in the same composition or in separate compositions.

In a particular embodiment, the nucleic acid molecules of the instant invention are delivered (e.g., via infection, transfection, electroporation, etc.) and expressed in cells via a vector (e.g., a plasmid), particularly a viral vector. The expression vectors of the instant invention may employ a strong promoter, a constitutive promoter, and/or a regulated promoter. Examples of promoters are well known in the art and include, but are not limited to, RNA polymerase II promoters, the T7 RNA polymerase promoter, and RNA polymerase III promoters (e.g., U6 and H1; see, e.g., Myslinski et al. (2001) Nucl. Acids Res., 29:2502-09). Examples of expression vectors for expressing the molecules of the invention include, without limitation, plasmids and viral vectors (e.g., adeno-associated viruses (AAVs), adenoviruses, retroviruses, and lentiviruses).

In a particular embodiment, the guide RNA of the instant invention may comprise separate nucleic acid molecules. For example, one RNA specifically hybridizes to a target sequence (crRNA) and another RNA (trans-activating crRNA (tracrRNA)) which specifically hybridizes with the crRNA. In a particular embodiment, the guide RNA is a single molecule (sgRNA) which comprises a sequence which specifically hybridizes with a target sequence (crRNA) and a tracrRNA sequence (scaffold sequence). Examples of gRNA scaffold sequences are well known in the art (e.g., 5'-GUUUUAGAGC UAGAAAUAGC AAGUUAAAAU AAGGCUAGUC CGUUAUCAAC UUGAAAAAGU GGCACCGAGU CGGUGCUUUU; SEQ ID NO: 10). As used herein, the term "specifically hybridizes" does not mean that the nucleic acid molecule needs to be 100% complementary to the target sequence. Rather, the sequence may be at least 80%, 85%, 90%, 95%, 97%, 99%, or 100% complementary to the target sequences. The greater the complementarity reduces the likelihood of undesired cleavage events at other sites of the genome. In a particular embodiment, the region of complementarity (e.g., between a guide RNA and a target sequence) is at least about 10, at least about 15, at least about 20, at least about 25, at least about 30, at least about 35, or more nucleotides. In a particular embodiment, the region of complementarity (e.g., between a guide RNA and a target sequence) is about 15 to about 25 nucleotides, about 15 to about 23 nucleotides, about 18 to about 23 nucleotides, about 19 to about 22 nucleotide, or about 20 or 21 nucleotides. In a particular embodiment, the guide RNA targets a sequence or comprises a sequence as set forth in the Examples or Figures provided herein.

In a particular embodiment, the guide RNA targets a sequence selected from the group consisting of:

```
                             (SEQ ID NO: 5)
CCAGGGGGCGTGCGGCAGCG;

(SEQ ID NO: 6)
GCAGCGCGGCGGCGGCGG (SEQ ID NO: 7)
AGGTGGGCTGCGGGCGCTCG;

(SEQ ID NO: 17)
CCGCCGCCGCCGCCGCCGCCG;

(SEQ ID NO: 18)
GGCGGCGGCGGCGGCGGCGG;

(SEQ ID NO: 19)
GGCAGCGCGGCGGCGGCGGCGG;

(SEQ ID NO: 20)
GGCCCAGCCGCCGCCGCCG.
```

The sequences may be extended or shortened by 1, 2, 3, 4, or 5 nucleotides at the end of the sequence opposite from the PAM (i.e., the 5' end). When the sequence is extended the added nucleotides should correspond to the FMR1 sequence (see, e.g., FIG. 2). In a particular embodiment, when two guide RNAs are used, one of the guide RNAs targets SEQ ID NO: 7.

In a particular embodiment, the guide RNA comprises a sequence selected from the group consisting of:

```
                             (SEQ ID NO: 16)
CCAGGGGGCGUGCGGCAGCG;

(SEQ ID NO: 14)
GCAGCGCGGCGGCGGCGG;

(SEQ ID NO: 15)
AGGUGGGCUGCGGGCGCUCG;

(SEQ ID NO: 21)
CCGCCGCCGCCGCCGCCGCCG;

(SEQ ID NO: 22)
GGCGGCGGCGGCGGCGGCGG;

(SEQ ID NO: 23)
GGCAGCGCGGCGGCGGCGGCGG;

(SEQ ID NO: 24)
GGCCCAGCCGCCGCCGCCG.
```

The sequences may be extended or shortened by 1, 2, 3, 4, or 5 nucleotides at the end of the sequence opposite from the PAM (i.e., the 5' end). When the sequence is extended the added nucleotides should correspond to the FMR1 sequence (see, e.g., FIG. 2). In a particular embodiment, when two guide RNAs are used, one of the guide RNAs comprises SEQ ID NO: 15.

As stated hereinabove, the instant invention provides compositions and methods for the inhibition, treatment, and/or prevention of fragile X syndrome and related disorders. Indeed, the instant invention also encompasses guide RNAs of the instant invention, nucleic acid molecules (e.g., an expression vector or viral vector) encoding the guide RNAs, and compositions comprising the guide RNAs and/or nucleic acid molecules (e.g., an expression vector or viral vector) encoding the guide RNAs. In a particular embodiment, the composition and nucleic acid molecules (e.g., an expression vector or viral vector) encoding the guide RNAs contain or encode more than one guide RNA. Compositions comprising at least one nucleic acid described herein are also encompassed by the instant invention. In a particular embodiment, the composition comprises at least one guide RNA (e.g., a nucleic acid molecule encoding the guide RNA (e.g., an expression vector)) and at least one pharmaceutically acceptable carrier. The composition may further comprise at least one Cas9 (e.g., a nucleic acid molecule encoding Cas9) and/or at least one donor nucleic acid molecule. In a particular embodiment, a nucleic acid molecule encoding an activator Cas9 as described above is included, optionally with at least one other guide RNA. In a particular embodiment, all of the nucleic acid molecules are encoded within a single expression vector (e.g., viral vector). Alternatively, the other nucleic acid molecules may be contained within a separate composition(s) with at least one pharmaceutically acceptable carrier. The present invention also encompasses kits comprising one or more of the above compositions. In a particular embodiment, the kit comprises a first composition comprising at least one guide RNA (e.g., a nucleic acid molecule encoding the guide RNA (e.g., an expression vector)) and a second composition comprising at least one Cas9 (e.g., a nucleic acid molecule encoding Cas9) and/or at least one donor nucleic acid molecule. In a particular embodiment, the kit comprises a first composition comprising at least one guide RNA (e.g., a nucleic acid molecule encoding the guide RNA (e.g., an expression vector)), at least one Cas9 (e.g., a nucleic acid molecule encoding Cas9), and/or at least one donor nucleic acid molecule and a second composition comprising a nucleic acid molecule (e.g., an expression vector) encoding an activator Cas9 as described above is included, optionally with at least one other guide RNA (e.g., a nucleic acid molecule encoding the guide RNA (e.g., an expression vector)). The compositions may further comprise at least one pharmaceutically acceptable carrier.

As explained hereinabove, the compositions of the instant invention are useful for treating, inhibiting, and/or preventing fragile X syndrome and related disorders. A therapeutically effective amount of the composition may be administered to a subject in need thereof. The dosages, methods, and times of administration are readily determinable by persons skilled in the art, given the teachings provided herein.

The components as described herein will generally be administered to a patient as a pharmaceutical preparation. The term "patient" or "subject" as used herein refers to human or animal subjects (including fetuses and embryos). The components of the instant invention may be employed therapeutically, under the guidance of a physician for the treatment of the indicated disease or disorder.

The pharmaceutical preparation comprising the components of the invention may be conveniently formulated for administration with an acceptable medium (e.g., pharmaceutically acceptable carrier) such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

Selection of a suitable pharmaceutical preparation depends upon the method of administration chosen. For example, the components of the invention may be administered by direct injection into any desired tissue (e.g., brain) or into the surrounding area. In this instance, a pharmaceutical preparation comprises the components dispersed in a medium that is compatible with blood or the target tissue.

The therapy may be, for example, administered parenterally, by injection into the blood stream (e.g., intravenous), or by subcutaneous, intramuscular or intraperitoneal injection. Pharmaceutical preparations for injection are known in the art. If injection is selected as a method for administering the therapy, steps must be taken to ensure that sufficient amounts of the molecules reach their target cells to exert a biological effect.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the antibody in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Injectable suspensions may be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art.

The methods of the instant invention may further comprise monitoring the disease or disorder in the subject after administration of the composition(s) of the instant invention to monitor the efficacy of the method. For example, the subject may be monitored for characteristics of fragile X syndrome and related disorders.

Definitions

The singular forms "a," "an," and "the" include plural referents unless the context clearly dictates otherwise.

The terms "isolated" is not meant to exclude artificial or synthetic mixtures with other compounds or materials, or the presence of impurities that do not interfere with the fundamental activity, and that may be present, for example, due to incomplete purification, or the addition of stabilizers.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, preservative, antioxidant, solubilizer, emulsifier, adjuvant, excipient, bulking substances, auxilliary agent or vehicle with which an active agent of the present invention is administered.

Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described, for example, in "Remington's Pharmaceutical Sciences" by E. W. Martin.

The term "treat" as used herein refers to any type of treatment that imparts a benefit to a patient suffering from an injury, including improvement in the condition of the patient (e.g., in one or more symptoms), delay in the progression of the condition, etc.

As used herein, the term "prevent" refers to the prophylactic treatment of a subject who is at risk of developing a condition and/or sustaining an injury, resulting in a decrease in the probability that the subject will develop conditions associated with the injury.

A "therapeutically effective amount" of a compound or a pharmaceutical composition refers to an amount effective to prevent, inhibit, or treat a particular injury and/or the symptoms thereof. For example, "therapeutically effective amount" may refer to an amount sufficient to modulate the pathology associated traumatic brain injury in a patient.

As used herein, the term "subject" refers to an animal, particularly a mammal, particularly a human.

A "vector" is a genetic element, such as a plasmid, cosmid, bacmid, phage or virus, to which another genetic sequence or element (either DNA or RNA) may be attached so as to bring about the replication and/or expression of the attached sequence or element. A vector may be either RNA or DNA and may be single or double stranded. An "expression operons" refers to a nucleic acid segment that may possess transcriptional and translational control sequences, such as promoters, enhancers, translational start signals, polyadenylation signals, terminators, and the like, and which facilitate the expression of a polynucleotide or a polypeptide coding sequence in a host cell or organism.

The following examples describe illustrative methods of practicing the instant invention and are not intended to limit the scope of the invention in any way.

Example 1

The CGG trinucleotide repeat in the 5' untranslated region of the FMR1 gene is polymorphic in size. The American College of Medical Genetics classifies a normal allele as 5-44 CGG repeats, an intermediate allele as 45-54 CGG repeats, a premutation allele as 55-200 CGG repeats, and a full mutation as greater than 200 CGG repeats in length.

Carriers of an FMR1 premutation allele are at an increased risk of developing fragile X syndrome and related disorders such as Fragile X-associated Tremor/Ataxia Syndrome (FXTAS) and Fragile X-associated Primary Ovarian Insufficiency (FXPOI). The mechanisms that result in pathology are not fully understood, but molecular changes including increased FMR1 mRNA levels, reduced fragile X mental retardation protein (FMRP) levels, instability of the repeat during transmission, and intranuclear inclusions are well characterized. More specifically, FXTAS may be characterized by intention tremor, gait ataxia, memory problems, cognitive decline, brain atrophy, white matter lesions, and/or intranuclear inclusions throughout the brain. FXPOI may be characterized by irregular/absent menses, fertility issues, early estrogen deficiency, and/or premature menopause (e.g., before 40 years of age).

Individuals with an FMR1 full mutation are diagnosed with fragile X syndrome (FXS), the most common monogenic cause of intellectual disability (ID) and autism spectrum disorder (ASD). Many stereotypical physical and behavioral features are common in individuals with FXS such as intellectual disability, facial dysmorphia, macroorchidism, hyperextensible joints, and behavioral problems. The full mutation results in epigenetic silencing of the FMR1 gene (very little to no FMR1 mRNA and FMRP levels), CpG methylation of CGG repeat and promoter region, and heterochromatinization of the region, resulting in the hallmark fragile site observable by karyotyping.

FIG. 1 provides the DNA sequence of FMR1 targetable using CRISPR/Cas9. The underlined DNA sequence is downstream of promoter sequence and upstream of coding sequences. This region will have a high tolerance for modifications that result from gene editing.

FIG. 2 provides examples of designed gRNAs targeting the FMR1 trinucleotide repeat. Four gRNAs were designed to edit the FMR1 CGG repeat and proximal sites using the SpCas9 and modified SpCas9 nucleases. The bars correspond to the gRNA sequences with the PAM sequences downstream of the target sequence. The polymorphic trinucleotide repeat is predicted to be shortened by one or more of the designed gRNAs.

FIG. 3 provides designed gRNAs targeting the boundary region of the FMR1 trinucleotide repeat. Two gRNAs were designed that target the boundary between the FMR1 trinucleotide repeat and the non-repetitive sequence using SpCas9 and modified SpCas9 nucleases. The black bars correspond to the gRNA sequences with the PAM sequences downstream of the target sequences. These gRNAs are predicted to enrich for DNA cleavage within the CGG trinucleotide repeat and allow for several of the repeats (approximately 6) to be retained in the edited sequence.

FIGS. 4A and 4B provide data showing the deletion of the FMR1 trinucleotide repeat in HEK 293 cells. More specifically, gRNAs were transfected into HEK 293 cells (normal FMR1 repeat length) with either SpCas9 or SpCas9 (D10A). Briefly, HEK 293 cells were cultured in DMEM with 10% FBS. Linear polyethyleneimine (15 nmol; Polysciences, Warrington, Pa.; CAT 23966-2) was used to transfect 1 ug of plasmid DNA in $2\times10^5$ cells. Cells were cultured for 24 hours in 6.5 mm wells. Transfected cells were positively selected by 3 ug/ml puromycin (Life Technologies Inc., Carlsbad, Calif.) treatment for 48 hours. Following selection cells were cultured to confluency and then harvested for DNA.

DNA was isolated using phenol-chloroform extraction followed by ethanol precipitation by established protocols. One-hundred nanograms of genomic DNA was PCR amplified using the following conditions: 500 nM forward primer 5' GCT CAG CTC CGT TTC GGT TTC ACT TCC GGT 3 (SEQ ID NO: 11)', 500 nM reverse primer 5' AGC CCC GCA CTT CCA CCA CCA GCT CCT CCA 3' (SEQ ID NO: 12), 200 uMdNTPs, 1 unit polymerase. PCR was performed with an initial 95 degree denaturation for 5 minutes followed by 10 cycles of 95 degrees for 35 seconds, 64 degrees for 35 seconds, and 68 degrees for 4 minutes, then 24 cycles of 97 degrees for 35 seconds, 64 degrees for 35 seconds, and 68 degrees for 4 minutes and 20 seconds per cycle. PCR product was separated by size by gel electrophoresis (1.5% agarose) in TAE buffer at 100 volts for 1 hour. Samples were amplified and electrophoresed with two internal controls: a transfection control that shows amplification of the unedited target, and a NTC (no template control) that shows no amplification.

As seen in FIG. 4, a deletion was shown for cells transfected with the Upstream and Downstream gRNAs and SpCas9 that corresponds in size to the sequence length between the targeted DNA.

FIG. 5 provides data showing deletion of the FMR1 trinucleotide repeat in HEK 293 cells using SpCas9 (D10A). More specifically, gRNAs were transfected into HEK 293 cells (normal FMR1 repeat length) with SpCas9 (D10A). A deletion was shown for cells transfected with the CGG Target and CGG Boundary gRNAs.

FIG. 6 provides data showing deletion of the FMR1 trinucleotide repeat in human fibroblasts with a full mutation. More specifically, gRNAs were transfected into human dermal fibroblast cells with SpCas9. Briefly, fibroblast cells were cultured in MEM with 15% FBS. Neon® electroporation (Life Technologies, Inc.) was used to transfect 10 ug of plasmid DNA in $3\times10^5$ cells. Cells were cultured for 48 hours in 24 mm wells. Transfected cells were positively selected by 1 ug/ml of puromycin treatment for 48 hours. Following selection cells were expanded and harvested for DNA. DNA extraction and genetic analysis were performed as described above.

As seen in FIG. 6, a deletion was shown for cells transfected with the CCG Target and CGG Boundary gRNAs in fibroblast cells harboring a full mutation (GM05131; Coriell Institute for Medical Research, Camden, N.J.). A deletion was also shown for cells transfected with the CGG target and CGG boundary gRNAs in fibroblasts with a normal CGG repeat size (GM05399; Coriell Institute for Medical Research).

The CGG repeat locus was sequenced in fibroblast cells harboring the FMR1 full mutation. One of the two sequences mapped corresponds to deletion of the entire CGG repeat locus except for the sequence CGGCG, while retaining the remaining proximal sequence. The other sequence was determined to correspond to deletion of the entire CGG repeat locus except for seven CGG trinucleotides. This CGG repeat length falls within the American College of Medical Genetics classification of a normal FMR1 allele.

FIG. 7 provides gRNA sequences to target the FMR1 trinucleotide repeat. Many additional gRNAs can be generated that targeted the SpCas9 nuclease to the FMR1 trinucleotide repeat. The black bars correspond to the gRNA sequences with the PAM sequences downstream of the target sequence.

FIG. 8 provides gRNA sequences to target the FMR1 trinucleotide repeat using engineered SpCas9. gRNAs can be generated that take advantage of recently released engineered SpCas9. The black bars correspond to the gRNA sequences with the new PAM sequences downstream of the target sequence.

The results indicate that the CGG repeat locus on FMR1 is targeted for deletion by the CRISPR/Cas9 system. The guide RNAs that have shown editing to date include the upstream, downstream, CGG target, CCG target, CGG boundary, and CCG boundary sequences. Editing of this region with both the fully active Cas9 nuclease and the mutated Cas9 nickase has been shown. Further, the CGG repeat locus was sequenced in a cell line that was edited using the CCG target and CGG boundary guide RNAs. Two sequences showed almost complete deletion of the CGG repeat locus, but the DNA sequence proximal to this locus was unchanged. In one of the sequences all but 7 CGG repeats remained. Notably, 7 CGG repeats is considered by the American College of Medical Genetics to be a normal FMR1 allele.

Example 2

FIG. 9 provides examples of designed gRNAs targeting the FMR1 trinucleotide repeat. Three gRNAs were designed to edit the FMR1 CGG repeat and proximal sites using the SpCas9 and modified SpCas9 nucleases. The black bars correspond to the gRNA sequences. The sequences of the target sequences are provided and the PAM site at the gRNA binding site is provided.

The ability of the gRNAs to delete the FMR1 trinucleotide repeat in HEK 293 cells was tested. Briefly, gRNAs were transfected into HEK 293 cells (normal FMR1 repeat length) with SpCas9. As seen in FIG. 10, bands corresponding to deletions are present for cells transfected with the gRNAs Upstream & Downstream, Upstream Boundary & Downstream, and Upstream 2 (target of TGACGGAGGCGCCGCTGCCA (SEQ ID NO: 13) with GGG PAM; Park et al. (2015) Cell Reports 13:234-241) and Downstream, but not for the control gRNA.

The ability of the gRNAs to delete the FMR1 trinucleotide repeats in human fibroblasts with a premutation or a full mutation was tested. Fibroblasts were transfected by electroporation. FIG. 11A shows bands corresponding to deletions for fibroblasts with a premutation transfected with the gRNAs Upstream & Downstream, Upstream Boundary & Downstream, and Upstream 2 and Downstream, but not for the control gRNA. Similarly, FIG. 11B shows bands corresponding to deletions for fibroblasts with a full mutation transfected with the gRNAs Upstream & Downstream, Upstream Boundary & Downstream, and Upstream 2 and Downstream, but not for the control gRNA.

The CGG repeat locus was sequenced in HEK 293 cells transfected with the Upstream Boundary (GCAGCGCGGCGGCGGCGG; SEQ ID NO: 14) and Downstream (AGGUGGGCUGCGGGCGCUCG; SEQ ID NO: 15) gRNAs. These sequences mapped to the targeted CGG repeat locus. As seen in FIG. 12A, partial or complete deletion of the CGG repeats is seen and, in one instance, the insertion of 5 nucleotides within the deleted sequence. The CGG repeat locus was also sequenced in HEK 293 cells transfected with the Upstream (CCAGGGGGCGUGCGGCAGCG; SEQ ID NO: 16) and Downstream (AGGUGGGCUGCGGGCGCUCG; SEQ ID NO: 15) gRNAs. These sequences mapped to the targeted CGG repeat locus. As seen in FIG. 12B, partial or complete deletion of the CGG repeats is seen.

FMR1 gene expression in HEK 293 cells was measured (by measuring mRNA levels) after editing with the gRNAs identified above. Notably, FMR1 expression in HEK 293 cells edited by Upstream Boundary and Downstream gRNAs, Upstream and Downstream gRNAs, and Upstream 2 and Downstream gRNAs was similar to cells transfected with a control gRNA. This indicates that the cleavage events did not adversely affect FMR1 expression. Similar results were obtained in a fibroblast cell line with a premutation.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for inhibiting, treating, and/or preventing a fragile X syndrome or a related disorder in a subject in need thereof, wherein said fragile X syndrome or related disorder is caused by a mutant CGG repeat within the 5' untranslated region of the Fragile X Mental Retardation 1 (FMR1) gene, wherein said mutant CGG repeat comprises at least 55 CGG repeats, said method comprising administering to the subject a nucleic acid molecule encoding Cas9 and two guide RNAs, thereby reducing the number of CGG repeats in the 5' untranslated region of the FMR1 gene in said subject, wherein said guide RNAs comprise a targeting sequence which is completely complementary to a sequence in the 5' untranslated region of the FMR1 gene, and wherein one guide RNA comprises a targeting sequence which is completely complementary to a sequence completely within the CGG repeats, wherein said related disorder is Fragile X-associated Tremor/Ataxia Syndrome (FXTAS) or Fragile X-associated Primary Ovarian Insufficiency (FXPOI), wherein at least one of the guide RNAs comprises a targeting sequence which is completely complementary to a sequence selected from the group consisting of CCAGGGGGCGTGCGGCAGCG (SEQ ID NO: 5); GCAGCGCGGCGGCGGCGG (SEQ ID NO: 6); AGGTGGGCTGCGGGCGCTCG (SEQ ID NO: 7); CCGCCGCCGCCGCCGCCGCCG (SEQ ID NO: 17); GGCGGCGGCGGCGGCGGCGG (SEQ ID NO: 18); GGCAGCGCGGCGGCGGCGGCGG (SEQ ID NO: 19); and
GGCCCAGCCGCCGCCGCCG (SEQ ID NO: 20).

2. The method of claim 1, wherein said subject has a premutation allele of the 5' untranslated region of the FMR1 gene.

3. The method of claim 1, wherein said subject has a full mutation allele of the 5' untranslated region of the FMR1 gene.

4. The method of claim 1, wherein said method comprises reducing the number of CGG repeats to 44 or fewer repeats.

5. The method of claim 1, wherein said method further comprises administering at least one donor DNA.

6. The method of claim 1, wherein said method further comprises administering a nucleic acid molecule encoding a fusion protein comprising an inactive Cas9 and a transcription activator peptide or protein.

7. The method of claim 1, wherein said guide RNA are administered as a nucleic acid molecule encoding said guide RNA.

8. The method of claim 1, wherein said nucleic acid molecules are administered in an expression vector.

9. The method of claim 8, wherein said expression vector is a viral vector.

10. The method of claim 1, wherein one guide RNA comprises a targeting sequence which is completely complementary to a sequence completely within the CGG repeats and one guide RNA comprises a targeting sequence which is completely complementary to a sequence 3' of the CGG repeats.

11. The method of claim 1, wherein one of the guide RNAs comprises a targeting sequence which is completely complementary to AGGTGGGCTGCGGGCGCTCG (SEQ ID NO: 7).

12. The method of claim 1, wherein said Cas9 is *Streptococcus pyogenes* Cas9 or *Streptococcus pyogenes* Cas9 D10A.

13. The method of claim 1, wherein one guide RNA comprises a targeting sequence which is completely complementary to a sequence completely within the CGG repeats and one guide RNA comprises a targeting sequence which is completely complementary to the 5' or 3' boundary of the CGG repeats.

14. A method for reducing the number of CGG repeats in a mutant CGG repeat within the 5' untranslated region of the Fragile X Mental Retardation 1 (FMR1) gene in a cell, wherein the mutant CGG repeat comprises at least 55 CGG repeats, said method comprising delivering to the cell a nucleic acid molecule encoding Cas9 and two guide RNAs, wherein said guide RNAs comprise a targeting sequence which is completely complementary to a sequence in the 5' untranslated region of the FMR1 gene, and wherein one guide RNA comprises a targeting sequence which is completely complementary to a sequence completely within the CGG repeats, wherein at least one of the guide RNAs comprises a targeting sequence which is completely complementary to a sequence selected from the group consisting of CCAGGGGGCGTGCGGCAGCG (SEQ ID NO: 5); GCAGCGCGGCGGCGGCGG (SEQ ID NO: 6); AGGTGGGCTGCGGGCGCTCG (SEQ ID NO: 7); CCGCCGCCGCCGCCGCCGCCG (SEQ ID NO: 17); GGCGGCGGCGGCGGCGGCGG (SEQ ID NO: 18); GGCAGCGCGGCGGCGGCGGCGG (SEQ ID NO: 19); and
GGCCCAGCCGCCGCCGCCG (SEQ ID NO: 20).

* * * * *